United States Patent
Winkler

(10) Patent No.: US 11,733,183 B2
(45) Date of Patent: Aug. 22, 2023

(54) IMAGING METHOD AND SYSTEM

(71) Applicant: DETECTION TECHNOLOGY OYJ, Oulu (FI)

(72) Inventor: Alex Winkler, Espoo (FI)

(73) Assignee: DETECTION TECHNOLOGY OYJ, Oulu (FI)

( * ) Notice: Subject to any disclaimer, the term of this patent is extended or adjusted under 35 U.S.C. 154(b) by 112 days.

(21) Appl. No.: 17/603,897

(22) PCT Filed: Apr. 15, 2020

(86) PCT No.: PCT/EP2020/060539
§ 371 (c)(1),
(2) Date: Oct. 14, 2021

(87) PCT Pub. No.: WO2020/212393
PCT Pub. Date: Oct. 22, 2020

(65) Prior Publication Data
US 2022/0196579 A1 Jun. 23, 2022

(30) Foreign Application Priority Data
Apr. 16, 2019 (EP) ..................................... 19169510

(51) Int. Cl.
*G01N 23/2206* (2018.01)
*A61N 5/10* (2006.01)
*G01N 23/05* (2006.01)
*G01N 33/28* (2006.01)
*G01T 1/24* (2006.01)

(52) U.S. Cl.
CPC ....... *G01N 23/2206* (2013.01); *A61N 5/1071* (2013.01); *G01N 23/05* (2013.01); *G01N 33/28* (2013.01); *G01T 1/24* (2013.01); *A61N 2005/109* (2013.01); *A61N 2005/1098* (2013.01)

(58) Field of Classification Search
CPC ... G01N 23/2206; G01N 23/05; A61N 5/1071
See application file for complete search history.

(56) References Cited

U.S. PATENT DOCUMENTS

| 2003/0155530 A1 | 8/2003 | Adnani et al. |
| 2004/0084626 A1* | 5/2004 | McGregor ................. G01T 3/08 250/370.13 |
| 2011/0035197 A1* | 2/2011 | Scoullar ............... G01V 5/0016 703/2 |

(Continued)

OTHER PUBLICATIONS

Extended European Search Report for Application 19169510.5, dated Sep. 25, 2019, 7 pages.

(Continued)

*Primary Examiner* — Hugh Maupin
(74) *Attorney, Agent, or Firm* — Lippes Mathias LLP

(57) ABSTRACT

It is an object to provide an imaging method and system. According to an embodiment, an imaging method comprises emitting neutrons into a material, wherein the material converts at least part of the emitted neutrons into a first plurality of gamma ray photons, and wherein at least part of the emitted neutrons pass through the material. Based on the neutrons passed through the material and the gamma ray photons, at least one property of the material can be deduced. An imaging method and an imaging system are provided.

15 Claims, 5 Drawing Sheets

(56) References Cited

U.S. PATENT DOCUMENTS

| | | | |
|---|---|---|---|
| 2011/0266643 A1* | 11/2011 | Engelmann | H01L 31/117 257/E31.087 |
| 2012/0148134 A1 | 6/2012 | McRae et al. | |
| 2013/0020661 A1* | 1/2013 | Orava | G01T 3/08 257/E31.127 |
| 2014/0077089 A1* | 3/2014 | Orava | G01T 3/06 250/370.05 |
| 2015/0287872 A1* | 10/2015 | Cauffiel | G01T 3/08 250/370.01 |

OTHER PUBLICATIONS

Do-Kun Yoon et al., "Tomographi image of prompt gamma ray from boron neutron capture therapy: A Monte Carlo simulation study", Applied Physics Letters 104, 083531 (2014), 4 pages.

International Search Report for Application No. PCT/EP2020/060539, dated Jul. 14, 2020, 4 pages.

\* cited by examiner

IMAGING METHOD AND SYSTEM

TECHNICAL FIELD

The present disclosure relates to imaging, and more particularly to an imaging system and an imaging method.

BACKGROUND

As neutrons interact with a material, the material may emit, amongst other radiation, gamma ray photons due to so-called neutron capture reactions. These gamma ray photons may leave their production material almost un-attenuated, if their energy is sufficiently high.

The number of specific neutron capture reactions, however, may be small in many materials. Thus, the signal generated by the gamma ray photons may be difficult to detect due to, for example, background and neutron induced background that may originate from other materials, present during measurement, or treatment. Therefore, it may be difficult to directly use these gamma ray photons for imaging applications, or other applications.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter.

It is an object to provide an imaging method and an imaging system. The foregoing and other objects are achieved by the features of the independent claims. Further implementation forms are apparent from the dependent claims, the description and the figures.

According to a first aspect an imaging method comprises: emitting neutrons into a material, wherein the material converts at least part of the emitted neutrons into a first plurality of gamma ray photons, and wherein at least part of the emitted neutrons pass through the material; converting at least part of the neutrons passed through the material into a second plurality of gamma ray photons; detecting a number of gamma ray photons, N1, in a first energy range, $B_1$, wherein the $B_1$ is comprised in a range 0-511 kiloelectronvolts, keV; detecting a number of gamma ray photons, $N_2$, in a second energy range, $B_2$, wherein the $B_2$ is comprised in a range 500-520 keV; detecting a number of gamma ray photons, $N_3$, in a third energy range, $B_3$, wherein the $B_3$ is comprised in a range 511-660 keV; detecting a number of gamma ray photons, $N_4$, in a fourth energy range, $B_4$, wherein a lower boundary of the $B_4$ is greater than or equal to 650 keV; and deducing at least one property of the material based on the $N_1$, the $N_2$, the $N_3$, and the $N_4$. Based on the $N_1$, the $N_2$, the $N_3$, and the $N_4$, it may be possible to, for example, efficiently image the material.

In an implementation form of the first aspect, the $B_1$ is comprised in a range 100-509 keV; the $B_2$ is comprised in a range 509-516 keV; the $B_3$ is comprised in a range 516-656 keV; and/or the lower boundary of the $B_4$ is greater than or equal to 656 keV. With such ranges, accuracy of the imaging of the material may be improved.

In a further implementation form of the first aspect, the $N_2$ corresponds to a number of annihilation events. Thus, the number of annihilation events may be deduced, which may provide additional information about the material.

In a further implementation form of the first aspect, the deducing at least one property of the material comprises: identifying at least one element in the material based on the $N_1$, the $N_2$, the $N_3$, and the $N_4$. Based on the at least one element, it may be possible to, for example, deduce other properties of the material.

In a further implementation form of the first aspect, the deducing at least one property of the material further comprises: deducing a concentration of the at least one element in the material based on the $N_1$, the $N_2$, the $N_3$, and the $N_4$. Based on the concentration of the at least one element, it may be possible to, for example, deduce other properties of the material.

In a further implementation form of the first aspect, the deducing at least one property of the material comprises: deducing a number of neutrons passed through the material based on $N_3$. Based on the number of neutrons passed through the material, for example, concentration of various elements in the material may be deduced.

In a further implementation form of the first aspect, the material comprises boron-10, and the deducing at least one property of the material comprises: deducing a boron-10 concentration in the material based on the $N_1$, the $N_2$, the $N_3$, and the $N_4$. Thus, it may be possible to efficiently deduce the boron-10 concentration in the material.

In a further implementation form of the first aspect, the imaging method further comprises: calculating a radiation dosage to a tumour in a patient for boron neutron capture therapy based on the boron-10 concentration. Thus, it may be possible to calculate the radiation dosages for the treatment with a reduced delay from the administration of the delivery agent, or with higher accuracy than currently possible.

In a further implementation form of the first aspect, at least one property of the material comprises a structural property of the material. Thus, the imaging method may be used for, for example, non-destructive testing (NDT).

In a further implementation form of the first aspect, the material comprises oil, and the deducing at least one property of the material comprises: deducing a chemical composition of the oil based on the $N_1$, the $N_2$, the $N_3$, and the $N_4$. Thus, the imaging method may be used for, for example, oil pipe inspection.

In a further implementation form of the first aspect, the converting at least part of the neutrons passed through the material into the second plurality of gamma ray photons is performed using a detector comprising cadmium. When the detector comprises cadmium, it may be possible to convert the neutrons into gamma ray photons with high efficiency.

In a further implementation form of the first aspect, the detector comprises at least one of: cadmium telluride; cadmium zinc telluride; cadmium magnesium telluride; and cadmium zinc telluride selenide. When the detector comprises at least one of these materials, it may be possible to convert the neutrons into gamma ray photons and then convert the gamma ray photons into electron-hole pairs in the same material. The detector signal may then be generated through the movement of the electron-hole pairs.

According to a second aspect, an imaging system comprises: a neutron source, configured to: emit neutrons into a material, wherein the material converts at least part of the emitted neutrons into a first plurality of gamma ray photons, and wherein at least part of the emitted neutrons pass through the material; a detector, configured to: convert at least part of the neutrons passed through the material into a second plurality of gamma ray photons; detect a number of gamma ray photons, $N_1$, in a first energy range, $B_1$, wherein the $B_1$ is comprised in a range 0-511 kiloelectronvolts, keV; detect a number of gamma ray photons, $N_2$, in a second energy range, $B_2$, wherein the $B_2$ is comprised in a range 500-520 keV; detect a number of gamma ray photons, $N_3$, in a third energy range, $B_3$, wherein the $B_3$ is comprised in a range 511-660 keV; and detect a number of gamma ray photons, $N_4$, in a fourth energy range, $B_4$, wherein a lower boundary of the $B_4$ is greater than or equal to 650 keV; and a computing device, configured to: deduce at least one property of the material based on the $N_1$, the $N_2$, the $N_3$, and the $N_4$. With these configurations, the imaging system may be able to, based on the $N_1$, the $N_2$, the $N_3$, and the $N_4$, efficiently image the material.

In an implementation form of the second aspect, the detector comprises a direct conversion material, comprising cadmium. With these configurations, the detector may be able to convert the neutrons into gamma ray photons with high efficiency.

In a further implementation form of the second aspect the direct conversion material comprises at least one of: cadmium telluride; cadmium zinc telluride; cadmium magnesium telluride; and cadmium zinc telluride selenide. When the direct conversion material comprises at least one of these elements, the direct conversion material may be able to convert neutrons into gamma ray photons and then convert the gamma ray photons into electron-hole pairs.

It is to be understood that the implementation forms of the second aspect described above may be used in combination with each other. Several of the implementation forms may be combined together to form a further implementation form.

Many of the attendant features will be more readily appreciated as they become better understood by reference to the following detailed description considered in connection with the accompanying drawings.

DESCRIPTION OF THE DRAWINGS

In the following, example embodiments are described in more detail with reference to the attached figures and drawings, in which.

In the following, identical reference signs refer to identical or at least functionally equivalent features.

DETAILED DESCRIPTION

In the following description, reference is made to the accompanying drawings, which form part of the disclosure, and in which are shown, by way of illustration, specific aspects in which the present disclosure may be placed. It is understood that other aspects may be utilized and structural or logical changes may be made without departing from the scope of the present disclosure. The following detailed description, therefore, is not to be taken in a limiting sense, as the scope of the present disclosure is defined be the appended claims.

For instance, it is understood that a disclosure in connection with a described method may also hold true for a corresponding device or system configured to perform the method and vice versa. For example, if a specific method step is described, a corresponding device may include a unit to perform the described method step, even if such unit is not explicitly described or illustrated in the figures. On the other hand, for example, if a specific apparatus is described based on functional units, a corresponding method may include a step performing the described functionality, even if such step is not explicitly described or illustrated in the figures. Further, it is understood that the features of the various example aspects described herein may be combined with each other, unless specifically noted otherwise.

Figure 1:
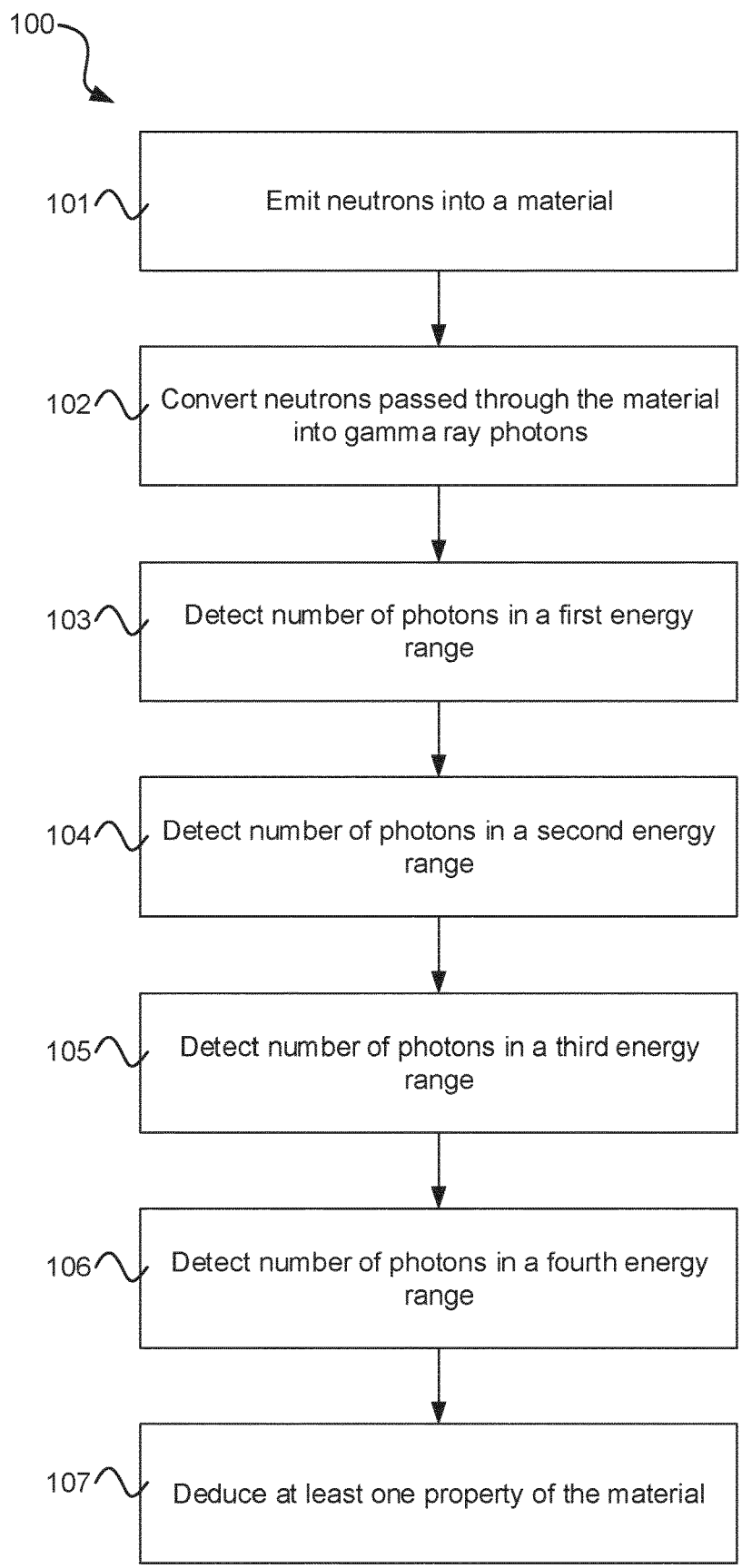
FIG. 1 illustrates a schematic flow chart of an imaging method according to an embodiment.

FIG. 1 illustrates a schematic flow chart of an imaging method 100 according to an embodiment. Herein, the imaging method 100 may be referred to as the method 100.

According to an embodiment, the imaging method 100 comprises emitting 101 neutrons into a material, wherein the material converts at least part of the emitted neutrons into a first plurality of gamma ray photons, and wherein at least part of the emitted neutrons pass through the material. The imaging method 100 may further comprise converting 102 at least part of the neutrons passed through the material into a second plurality of gamma ray photons.

According to an embodiment, the imaging method 100 may further comprise detecting 103 a number of gamma ray photons, $N_1$, in a first energy range, $B_1$, wherein the $B_1$ is comprised in a range 0-511 kiloelectronvolts, keV.

The imaging method 100 may further comprise detecting 104 a number of gamma ray photons, $N_2$, in a second energy range, $B_2$, wherein the $B_2$ is comprised in a range 500-520 keV.

The imaging method 100 may further comprise detecting (105) a number of gamma ray photons, $N_3$, in a third energy range, $B_3$, wherein the $B_3$ is comprised in a range 511-660 keV.

The imaging method 100 may further comprise detecting 106 a number of gamma ray photons, $N_4$, in a fourth energy range, $B_4$, wherein a lower boundary of the $B_4$ is greater than or equal to 650 keV.

The imaging method 100 may further comprise deducing 107 at least one property of the material based on the $N_1$, the $N_2$, the $N_3$, and the $N_4$.

As a person skilled in the art can appreciate, the steps 101-107 in the imaging method 100 may be performed in any order, or some, or all steps may be performed substantially simultaneously.

According to an embodiment, the deducing at least one property of the material comprises identifying at least one element in the material based on the $N_1$, the $N_2$, the $N_3$, and the $N_4$.

According to another embodiment, the deducing at least one property of the material further comprises: deducing a concentration of the at least one element in the material based on the $N_1$, the $N_2$, the $N_3$, and the $N_4$.

Herein, the term "element" may refer to, for example, a chemical element, an isotope, or a chemical compound, comprising more than one element.

According to another embodiment, the deducing at least one property of the material comprises: deducing a number of neutrons passed through the material based on $N_3$.

According to another embodiment, the converting at least part of the neutrons passed through the material into the second plurality of gamma ray photons is performed using a detector comprising cadmium. For example, the detector may comprise at least one of: cadmium telluride; cadmium zinc telluride; cadmium magnesium telluride; and cadmium zinc telluride selenide.

The use of the $N_1$, the $N_2$, the $N_3$, the $N_4$ in the imaging method 100 may provide improved imaging. Since the photon counts may comprise different energy intervals, it may be possible to identify various elements in the material. Furthermore, information from both the number of neutrons passed through the material and number of gamma ray photons may be utilised in the method to provide more information about the material.

Figure 2A:
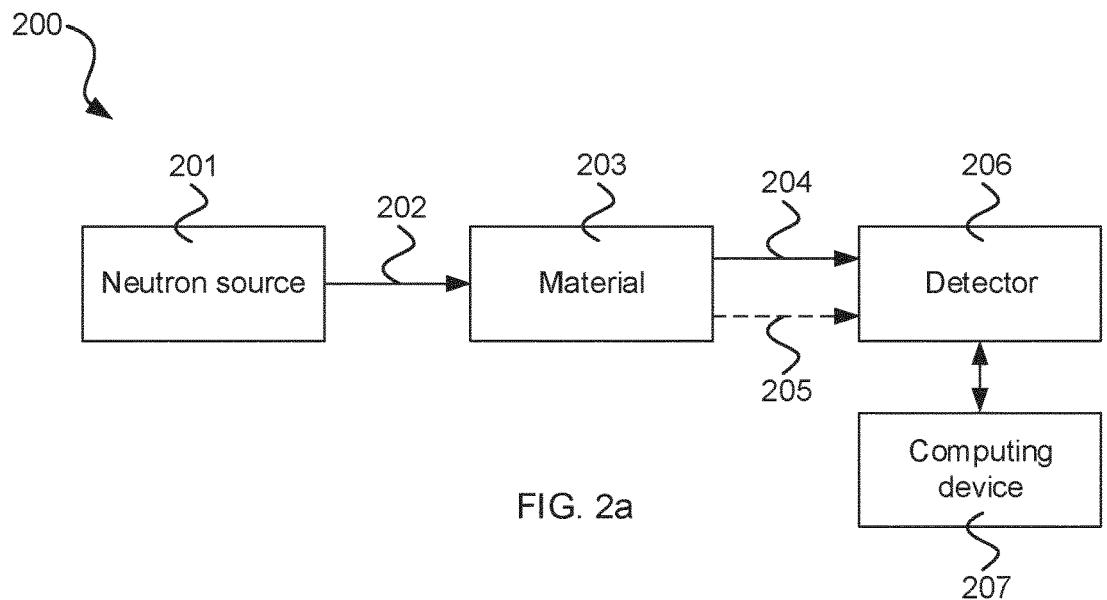
FIGS. 2a-2c illustrate schematic representations of imaging systems according to the embodiments.

FIG. 2a illustrates a schematic representation of an imaging system 200 according to an embodiment. A neutron source 201 may emit neutrons 202 into a material 203. In response to the neutrons 202, the material may emit photons 205. The photons 205 may comprise, for example, gamma ray photons. Furthermore, some neutrons 204 may pass through the material 203. The passed through neutrons 204 and/or the photons may be detected by a detector 206. The detector 206 may be coupled to a computing device 207. Alternatively, the detector 206 may comprise a computing device 207.

According to an embodiment, the imaging system 200 comprises a neutron source 201. The neutron source 201 may be configured to emit neutrons 202 into a material 203. The material 203 may convert at least part of the emitted neutrons 202 into a first plurality of gamma ray photons 205. At least part 204 of the emitted neutrons may pass through the material 203.

The imaging system may further comprise a detector 206. The detector 206 may be configured to convert at least part of the neutrons passed through the material 204 into a second plurality of gamma ray photons.

The detector 206 may be further configured to detect a number of gamma ray photons, $N_1$, in a first energy range, $B_1$, wherein the $B_1$ is comprised in a range 0-511 kiloelectronvolts, keV.

The detector 206 may be further configured to detect a number of gamma ray photons, $N_2$, in a second energy range, $B_2$, wherein the $B_2$ is comprised in a range 500-520 keV.

The detector 206 may be further configured to detect a number of gamma ray photons, $N_3$, in a third energy range, $B_3$, wherein the $B_3$ is comprised in a range 511-660 keV.

The detector 206 may be further configured to detect a number of gamma ray photons, $N_4$, in a fourth energy range, $B_4$, wherein a lower boundary of the $B_4$ is greater than or equal to 650 keV.

The imaging system 200 may further comprise a computing device 207. The computing device 207 may be configured to deduce at least one property of the material 203 based on the $N_1$, the $N_2$, the $N_3$, and the $N_4$. The computing device 207 may be electrically coupled to the detector 206.

The detector 206 may be configured to count photons. As a person skilled in the art can appreciate, the detector 206 does not need to be configured to count all individual photons. Instead, the detector 206 may comprise some counting efficiency. The counting efficiency may be determined by the quantum efficiency of the detector 206 and any electrical losses in the detector 206. Quantum efficiency may quantify the efficiency at which the detector 206 is able to convert absorbed photons into electron-hole pairs.

The detector 206 may comprise pixels. Each pixel may be configured to detect gamma ray photons and/or neutrons as disclosed herein.

Some components of the detector 206 and/or computing device 207 may be configured to be resistant to damage or malfunctions caused ionising radiation, such as neutron radiation. Such components may be referred to as radiation hardened.

In some cases, two or more gamma ray photons may be detected by the detector 206 almost simultaneously. In such a situation, the detector 206 may not be able to recognise these photons as separate events. This may be referred to as pile-up. The detector 206 may be configured to use some means of pile-up rejection to mitigate this effect.

The computing device 207 may comprise at least one processor. The at least one processor may comprise, for example, one or more of various processing devices, such as a co-processor, a microprocessor, a controller, a digital signal processor (DSP), a processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, or the like.

The computing device 207 may further comprise a memory. The memory may be configured to store, for example, computer programs and the like. The memory may comprise one or more volatile memory devices, one or more non-volatile memory devices, and/or a combination of one or more volatile memory devices and non-volatile memory devices. For example, the memory may be embodied as magnetic storage devices (such as hard disk drives, floppy disks, magnetic tapes, etc.), optical magnetic storage devices, and semiconductor memories (such as mask ROM, PROM (programmable ROM), EPROM (erasable PROM), flash ROM, RAM (random access memory), etc.).

As a person skilled in the art can appreciate, when the computing device 207 is configured to implement some functionality, some component and/or components of the computing device 207, such as the at least one processor and/or the memory, may be configured to implement this functionality. Furthermore, when the at least one processor is configured to implement some functionality, this functionality may be implemented using program code comprised, for example, in the memory.

The computing device 207 may be configured to implement charge sharing correction using any produce known in the art, such as deconvolution. This may reduce diffusion of the photoelectric charge between neighbouring pixels in the detector 206. Charge sharing can induce a low-energy tail in the measured spectra and can be particularly significant for small pixel sizes. The charge sharing correction may improve the energy resolution of the detector 206.

Herein, the terms "gamma ray", "gamma ray photon", or similar may refer to electromagnetic radiation with photon energy more than 100 kiloelectronvolts (keV), independent of the origin of the photon.

Figure 2B:
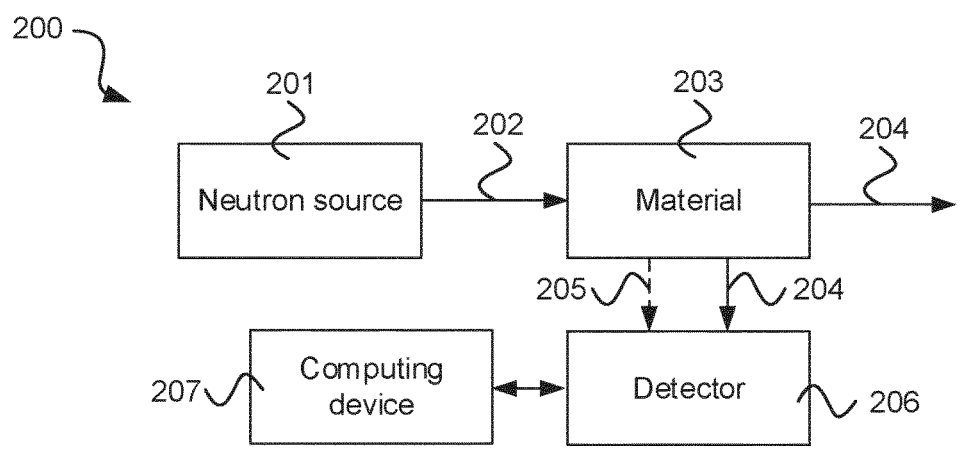

FIG. 2b illustrates a schematic representation of the imaging system 200 according to another embodiment. As is illustrated in the embodiment of FIG. 2b, not all of the passed through neutrons 204 may be captured by the detector 206. Instead, depending on the positioning of the neutron source 201 and the detector 206, some fraction of the passed through neutrons 204 may not be captured by the detector 206. The embodiment of FIG. 2b may be used, for example in boron neutron capture therapy.

Figure 2C:
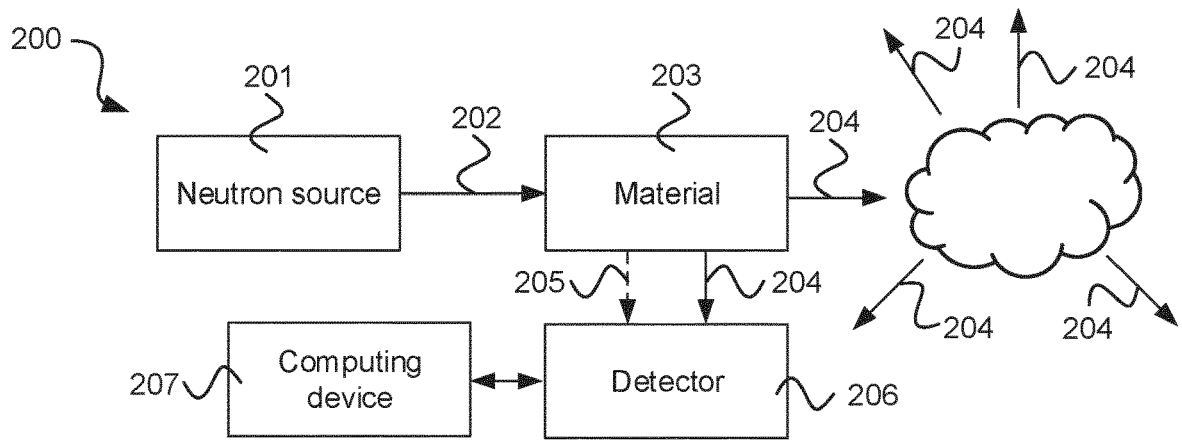

FIG. 2c illustrates a schematic representation of the imaging system 200 according to another embodiment. As is illustrated in the embodiment of FIG. 2c, the passed through neutrons 204 may scatter, for example in air, after passing through the material 203. Such scattering may be random. Thus, some neutrons 204 may travel in non-linear paths before being absorbed by the detector 206.

Figure 3:
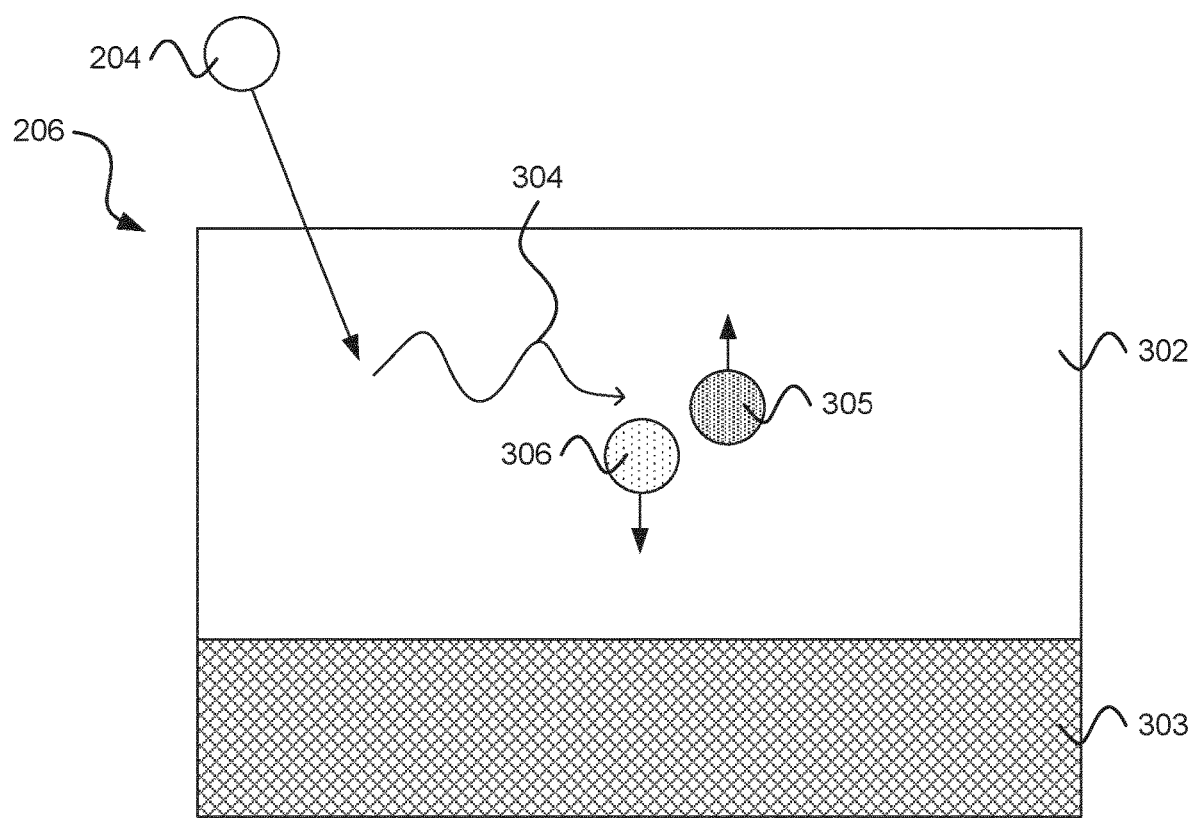
FIG. 3 illustrates a schematic representation of a detector comprised in the imaging system according to an embodiment.

FIG. 3 illustrates a schematic representation of the detector 206 according to an embodiment. The detector 206 may comprise a direct conversion material 302 and an application specific integrated circuit (ASIC) 303 that is electrically coupled to the detector.

The direct conversion material 302 may comprise cadmium (Cd). For example, the direct conversion material 302 may comprise cadmium-113 ($^{113}$Cd). The direct conversion material 302 may also comprise tellurium (Te). The direction conversion material 302 may comprise a compound semiconductor, such as cadmium telluride (CdTe), cadmium zinc telluride (CdZnTe), cadmium magnesium telluride (CdMgTe), or cadmium zinc telluride selenide (CdZnTeSe).

In some embodiments, the direct conversion material 302 may be arranged as a layer. The detector 206 may further comprise other layers. The direct conversion material 302 may be referred to as direct conversion layer. Alternatively, the direct conversion material 302 may be arranged into various other shapes/arrangements.

The direct conversion material 302 may be configured to convert incident neutrons 204 into gamma ray photons 304. The incident neutrons 204 may be those that passed through the material 203. The direct conversion material 302 may be further configured to convert the gamma ray photons 304 into pairs of electrons 306 and holes 305, also referred to as electron-hole pairs. Furthermore, the direct conversion material 302 may be configured to convert any other gamma ray photons, such the gamma ray photons 205 generated in the material 203, into pairs of electrons 306 and holes 305.

The electrons 306 and holes 305 may be separated by a voltage applied over the direct conversion material 302. Thus, the electrons 306 may be detected by the ASIC 303. Thus, the detector 206 may be configured to detect both neutrons 204 and gamma ray photons 205, at the same time.

The ASIC 303 and/or the direct conversion material 302 may comprise pixels. Each pixel may be configured to detect incident neutrons 204 and/or gamma ray photons 205 at the location of the pixel. Thus, the detector 206 may detect the spatial distribution of the neutrons 204 passed through the material 203 and/or of the gamma ray photons 205 emitted by the material. Each pixel may convert the intensity value to, for example, a voltage or a current.

Figure 4:
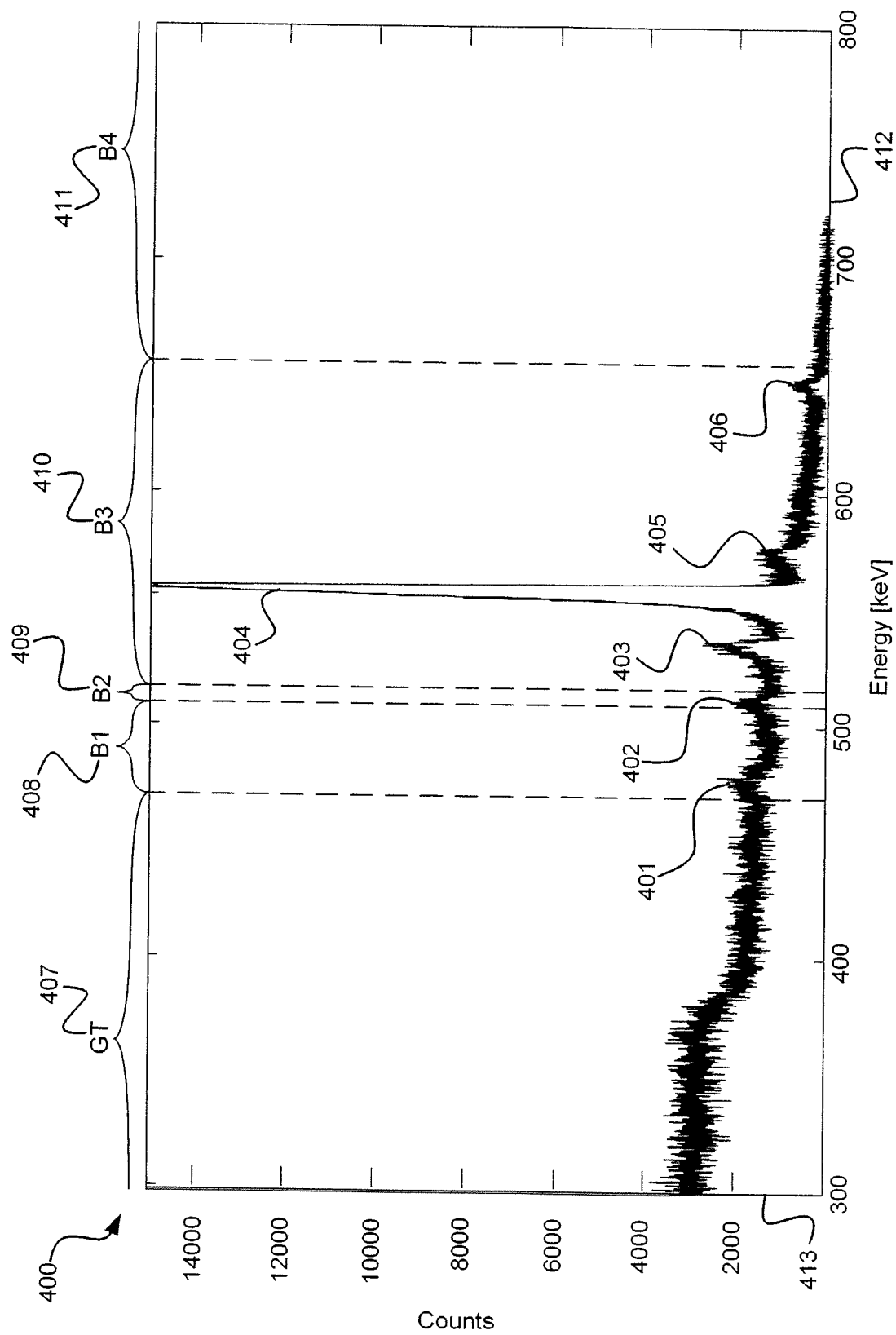
FIG. 4 illustrates a schematic representation of a spectrum according to an embodiment.

FIG. 4 illustrates a schematic representation of a spectrum 400 according to an embodiment. The spectrum 400 represents a photon count 413 as a function of photon energy 412.

In the embodiment of FIG. 4, the spectrum 400 may be generated by the detector 206. For example, the neutron source 201 may emit neutrons 202 into the material 203, and the material 203 may comprise boron-10 ($^{10}$B). The detector 206 may comprise Cd. The detector may be similar to the embodiment of FIG. 3. Each pixel in the detector 206 may be configured to generate a spectrum 400.

The peak 401 at approximately 478 keV in the spectrum 400 may be due to the following reaction in the material 203:

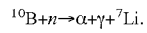

This reaction may be referred to as the boron neutron capture (BNC) reaction. As the $^{10}$B in the material 203 absorbs a neutron (n), an alpha particle (α), a gamma ray photon (γ) and a lithium-7 ($^{7}$Li) may be emitted. Energy of the gamma ray photon may be approximately 477.59 keV. As such gamma ray photons are absorbed by the detector 206, the peak 401 can be observed in the spectrum 400 at this energy.

The peak 402 at energy 511 keV in the spectrum 400 may comprise a so-called annihilation peak. A gamma ray photon may generate an electron-positron pair in the detector 206, if the energy of the gamma ray photon is above 1022 keV. The electron-positron pair may then annihilate and generate two gamma ray photons at energy 511 keV each. This may be referred to as an annihilation event. Thus, the corresponding peak 402 can be detected in the spectrum 400 at this energy.

The annihilation events may take place in the detector 206. For example, if the detector 206 comprises shielding which may comprise, for example, lead, high numbers of annihilation events may take place in such shielding. Annihilation events may also take place in any other part of the detector 206, such as the direct conversion material 302.

The peak 403 at energy 535 keV may be referred to as an escape peak. The 558 keV peak 404 may lose a photon energy through escape events. Escape events are lower than the initializing event. In the embodiment of FIG. 4, 558 keV−23 keV=535 keV. The energy loss of 23(.1) keV is due to a Cd$_{K\alpha}$ x-ray photon that was generated in the electron shell of a Cd atom and has later escaped. Thus, the corresponding peak 403 can be detected in the spectrum 400 at this energy.

Peak 404 at energy 558 keV may be due to the following reaction:

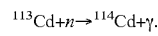

In this reaction, cadmium-113 ($^{113}$Cd) in the detector 206 may capture a neutron (n) and transmute into cadmium-114 ($^{114}$Cd). After the transmutation, the $^{114}$Cd may be in an excited state, and as the $^{114}$Cd relaxes, it may release a gamma ray photon at 558.46 keV. This gamma ray photon may be referred to as cadmium prompt gamma (CdPG). Thus, the peak 404 may be observed in the spectrum 400.

Herein, the term "prompt gamma" may refer to a gamma ray photon that is emitted during or substantially immediately after a fission event. This is in contrast to delayed gamma rays which may result from beta decay of fission products.

The cadmium reaction described above may also generate gamma ray photons at energies other than the 558.46 keV. For example, peak 405 at energy 576.08 keV and peak 406 at energy 651.26 keV may be due to gamma ray photons generated by the cadmium reaction described above. The peaks 405 and 406 may be referred to as minor emission peaks due to their small size compared to the peak 404. The peak 404 may be referred to as major emission peak.

Five energy ranges are illustrated in the embodiment of FIG. 4. A global threshold (GT) energy range 407 may cover energies from 0 keV to a first energy threshold. In the embodiment of FIG. 4, the first energy threshold may be approximately 470 keV. Alternatively, the GT energy range 407 may cover some subrange of this. The GT energy range 407 may comprise energy ranges that may not be of interest for a given application. For example, in the embodiment of FIG. 4 there may be no energy peaks of interest below 470 keV. Thus, the first energy threshold may be 470 keV.

A first energy range (B$_1$) 408 may cover an energy range from the first energy threshold to a second energy threshold. For example, in the embodiment of FIG. 4, the second energy threshold may be approximately 509 keV. Alternatively, the B$_1$ 408 may cover some subrange of this. Thus, in the embodiment of FIG. 4, B$_1$ 408 may comprise the 478 keV peak 402 described above. The first and second threshold, and therefore the energy range of B$_1$ 408, may vary depending on the material.

Number of photons detected in the $B_1$ may be referred to as $N_1$.

A second energy range ($B_2$) 409 may cover an energy range from the second energy threshold to a third energy threshold. In the embodiment of FIG. 4, the third energy threshold may be, for example, 516 keV. Thus, $B_2$ 409 may comprise the annihilation peak 402 described above.

Number of photons detected in the $B_2$ may be referred to as $N_2$.

In the imaging method 100 and/or in the imaging system 200, the annihilation events may be counted in order to make sure that the gamma ray photons generated in the BNC reaction can be distinguished from the gamma ray photons generated in the annihilations annihilation events. An efficient way of achieving this may be to counting both separately.

In some embodiments, the $N_2$ may be utilised in ways other than to distinguish the gamma ray photons generated in the BNC reaction from the gamma ray photons generated in the annihilation events. For example, the number of annihilation events may provide additional information about the material 203. For example, in PET imaging using fluorine-18 ($^{18}F$), the main emitter can be a beta particle, in particular a positron particle, which can annihilate in the body creating two 511 keV photons. In such a case, $N_2$ can be considered as a main signal and photon counts could be used as support signals to increase accuracy as described herein.

A third energy range ($B_3$) 410 may cover an energy range from the third energy threshold to a fourth energy threshold. In the embodiment, of FIG. 4, the fourth energy threshold may be, for example, 656 keV. Thus, $B_3$ 410 may comprise the peaks 403-406. Therefore, the total photon count in $B_3$ 410 may be used to count the number of CdPG reactions in the detector 206.

Number of photons detected in the $B_3$ may be referred to as $N_3$.

A fourth energy ranged ($B_4$) 411 may comprise an energy range from the third energy threshold onwards. Upper boundary of the $B_4$ 411 may be, for example, end of the spectrum 400. End of the spectrum 400 may be determined, for example, by the properties of the detector 206. For example, in the embodiment of FIG. 4, upper boundary of the $B_4$ 411 may be 800 keV.

Number of photons detected in the $B_4$ may be referred to as $N_4$.

The energy ranges described above in relation to the embodiment of FIG. 4 are only exemplary and may vary depending on the application. Especially the GT 407, the $B_1$ 408, and the $B_4$ 411 may vary depending on the material 203, since different reactions may take place when neutrons are emitted into different materials.

Figure 5:
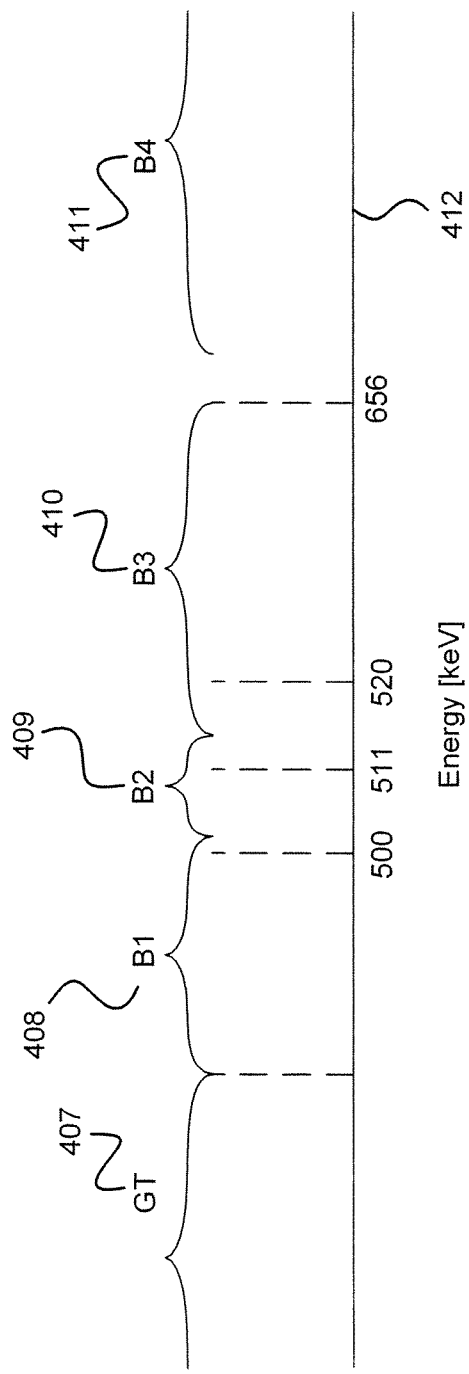
FIG. 5 illustrates a schematic representation of energy ranges according to an embodiment.

FIG. 5 illustrates a schematic representation of energy ranges according to an embodiment. The energy ranges and relations between the energy ranges presented in the embodiment of FIG. 5 are only exemplary. For example, some energy ranges may be presented as contiguous in the embodiment of FIG. 5. However, this may not be the case in all embodiments. Furthermore, some energy ranges may overlap even though such energy ranges may not be presented in the embodiment of FIG. 5.

The GT 407 may be comprised in the range 0-511 keV. The GT 407 may also be comprised in any subrange of this range. For example, the GT 407 may be comprised in the range 100-511 keV, 200-511 keV, or 100-400 keV.

The $B_1$ 408 may be comprised in the range 0-511 keV. The $B_1$ 408 may also be comprised in any subrange of this range. For example, the $B_1$ 408 may be comprised in the range 100-500 keV, 200-500 keV, 100-511 keV, 470-509 keV, or 300-511 keV. It should be appreciated that since $B_1$ 408 is an energy range, when $B_1$ 408 is comprised in some other range, $B_1$ 408 may comprise any subrange of this range. For example, if $B_1$ 408 is comprised in the range 0-511 keV, the $B_1$ 408 may correspond to, for example, the range 470-509 keV. In such a case, the detector 206 may be configured to detect gamma ray photons in the range 470-509 keV, and the method 100 may comprise detecting gamma ray photons in the range 470-509 keV. Similar remarks may apply to the GT 407, the $B_2$ 409, the $B_3$ 410, and/or the $B_4$ 411.

The $B_2$ 409 may be comprised in the range 500-520 keV. The $B_2$ 409 may also be comprised in any subrange of this range. For example, the $B_2$ 409 may be comprised in the range 505-515 keV, 509-516 keV, or 504-516 keV.

The $B_1$ 408 and the $B_2$ 409 may be contiguous. For example, the upper boundary of the B1 408 may be $E_1$, and the lower boundary of the B2 409 may be $E_1$. $E_1$ may be, for example, in the range 500-511 keV, 505-511 keV, or 509-511 keV.

The $B_3$ 410 may be comprised in the range 511-660 keV. The $B_3$ 410 may also be comprised in any subrange of this range. For example, the $B_3$ 410 may be comprised in the range 516-656 keV or 515-656 keV.

The $B_2$ 409 and the $B_3$ 410 may be contiguous. For example, the upper boundary of the $B_2$ 409 may be $E_2$, and the lower boundary of the $B_3$ 410 may be $E_2$. $E_2$ may be, for example, in the range 511-520 keV, 511-516 keV, or 511-513 keV.

The $B_3$ 410 may be comprised in the range 511-660 keV. The $B_3$ 410 may also be comprised in any subrange of this range. For example, the $B_3$ 410 may be comprised in the range 516-656 keV or 515-656 keV.

Lower boundary of the $B_4$ 411 may be in the range 650-670 keV. For example, the lower boundary of the $B_4$ 411 may be equal to or greater than 651 keV.

The $B_3$ 410 and the $B_4$ 411 may be contiguous. For example, the upper boundary of the $B_3$ 410 may be $E_3$, and the lower boundary of the $B_4$ 411 may be $E_3$. $E_3$ may be, for example, in the range 650-670 keV, 650-660 keV, or 652-658 keV.

In some embodiments, the energy ranges $B_1$-$B_4$ may not overlap. For example, the energy ranges $B_1$-$B_4$ may be contiguous. In some embodiments, the energy ranges $B_1$-$B_4$ may not be contiguous. For example, there may be so-called guard bands, or gaps between some of the energy ranges $B_1$-$B_4$.

According to an embodiment, information about the material can be extracted based on the $N_1$ and the $N_4$ or based on the $N_3$.

According to another embodiment, the information about the material can be extracted based on a change in $N_3$ compared to a change in $B_1$ and/or $B_4$. Such change can be, for example, compared to a reference value.

The $N_2$ can be used to assure that the $N_3$ only contains information about the CdPG reaction.

The imaging method 100 and/or the imaging system 200 may be utilised, for example, in boron neutron capture therapy (BNCT). BNCT is a radiation therapy against difficult tumours such as head, neck, or brain tumours. The imaging method 100 and/or the imaging system 200 may be used to calculate dosages to tumours and healthy tissue for a patient during BNCT.

According to an embodiment, the material 203 comprises boron-10, and the deducing at least one property of the material comprises: deducing a boron-10 concentration in the material based on the $N_1$, the $N_2$, the $N_3$, and the $N_4$. For example, the material 203 may comprise a tumour cell.

According to an embodiment, the imaging method 100 further comprises: calculating a radiation dosage to a tumour in a patient for boron neutron capture therapy based on the boron-10 concentration. The radiation dosage may be, for example, a neutron radiation dosage. Alternatively or additionally, the radiation dosage may comprise some other radiation dosage, such as those described herein. As a person skilled in the art can understand, a neutron radiation dosage may also comprise other radiation dosages.

Herein, the term "thermal neutron", "thermalized neutron" or similar may refer to a free neutron that has a kinetic energy corresponding to the average energy of the particles of ambient materials. The kinetic energy of a thermal neutron may be, for example, approximately 0.025 keV. This may correspond to a neutron speed of approximately 2000 metres per second (m/s) and to a neutron wavelength of about $2 \times 10^{-10}$ metres.

$^{10}$B can be made to accumulate in tumour cells of a patient using various procedures known in the art. For example, $^{10}$B can be made to accumulate in the tumour cells by administering a dosage of a delivery agent to the patient. Various delivery agents are known in the art. When these tumour cells comprising $^{10}$B are hit by thermalized neutrons, prompt gammas (PGs) can be generated via the BNC reaction described above. Herein, prompt gammas generated in this reaction may be referred to as boronPGs or bPGs. The bPGs are high energetic (478 keV) and leave the patient body nearly un-attenuated. Using the imaging method 100, these photons may be detected. A 3D reconstruction of the tumour may be generated for dosage calculations.

It should be noted that the number of bPGs from the BNC reaction can be very small. Especially in comparison to the background and neutron induced background, that can occur during the therapy. This background may also be originating from other materials present near the neutron beam.

The number of neutrons that are scattered out of the patient and are not converted by the $^{10}$B in the BNC reaction in the tumour can be related to the number of BNC reactions that took place in the tumour. The more BNC reactions take place in the tumour, the smaller the number of neutrons that get scattered out of the patient can be. As well as, vice versa: the fewer BNC reactions take place, the larger the number of neutrons that scatter out of the patient can be.

These neutrons can be detected using, for example, the detector 206 of embodiment of FIG. 3. Neutrons that are scattered out of the patient and are further scattered into the detector 206 can be converted inside the detector 206 into cadmium PGs. These PGs may be referred to as CdPGs. The energy of most of these CdPGs can be the aforementioned 558 keV. These CdPGs can be detected by the detector 206 with high efficiency, resulting in a peak at 558 keV as described above. The conversion of the neutrons to CdPGs as well as the conversion of CdPGs into electrical charges can occur within the same detector material and with high efficiency.

Furthermore, the number of scattered neutrons that reach detector 206 (and therefore the number of CdPGs) can be several orders of magnitudes larger than the number of bPGs from the BNC reaction.

The dose to healthy and tumour tissue in BNCT can be calculated based on the $N_1$, $N_2$, $N_3$, and $N_4$. This approach may allow a real time evaluation of the signal(s) during the therapy, as the flux of scattered neutrons towards the detector may be high enough for quick readout, but low enough to not saturate or damage the detector.

$N_1$ may correspond to the number of bPGs, and $N_3$ may correspond to the number of CdPGs. Naturally, $N_1$ may not be equal to the number of bPGs, and $N_3$ may not be equal to the number of CdPGs, since the detector 206 may comprise some efficiencies and/or inefficiencies at which the detector 206 can convert the PGs to electron-hole pairs.

Herein, when two quantities correspond to each other, there may be a correspondence between the quantities. For example, the quantities may be proportional or inversely proportional to each other.

The system 200 may utilise $N_2$ and $N_4$ in addition to $N_1$ and $N_3$ in order to obtain more accurate estimate of the $^{10}$B concentration. Since $N_2$ may correspond to the number of annihilation events, $N_2$ may be used to estimate the number of gamma ray photons incident on the detector 206, more accurately.

Dose calculation in BNCT may be performed, for example, using the following steps:
- An intensity map of the radioactive activity within the patient may be obtained during measurement
- The intensity map may be registered (combined) with a CT scan for anatomical reference. This may be optional.
- The number of nuclear reactions+end products can be calculated through the intensity map. In BNCT this number of nuclear reactions may correspond to the number of BNC reactions.
- Based on the number of nuclear reactions, the dose can then be estimated via comparison values published, for example, in the Medical Internal Radiation Dose (MIRD) database.

The number of nuclear reactions can be directly measured, through the BNC reaction and the subsequent 478 keV photon, and/or indirectly through the number of neutrons that did not convert in the BNC reaction.

Number of BNC reactions $N_{BNC}$ can be calculated using:

$$N_{BNC} = (N_n - N_{CdNC}) \times c,$$

where $N_n$ is the number of neutrons administered to the patient, $N_{CdNC}$ is the number of CdNC reactions, and c is a correction factor. c may account for the geometry of the detector 206, the therapy setup and position, and/or the patient specific details that may influence the measurement of the detector 206. These are only examples of considerations that c may account for and should not be considered as restrictive. c may also account for various other considerations.

The number of CdNC reaction can be determined using $N_3$. The $B_3$ can cover about 83% of all gamma emissions of the CdNC reaction up to 1000 keV. Therefore, an error of, for example, 17% may be possible.

The $B_4$ 411 can comprise several additional minor gamma emissions from the CdNC reaction. By adding these emissions to the intensity of the $B_3$ 410, the error of the CdNC reaction may be possible to be reduced to as low as 2.5%. This can lead to more accurate BNC reaction calculations and thus to more accurate dose calculations.

According to an embodiment, in the imaging method 100, the at least one property of the material comprises a structural property of the material. For example, the material may be part of a structure, such as an oil pipe, and the imaging method 100 may be used to perform non-destructive testing (NDT) on the structure. The structural property may comprise, for example, the structural integrity of the material.

According to another embodiment, in the imaging method 100, the material comprises oil, and the deducing at least one property of the material comprises: deducing a chemical composition of the oil based on the $N_1$, the $N_2$, the $N_3$, and the $N_4$. For example, the imaging method 100 may be used to deduce the chemical composition of oil inside and oil pipe.

For example, by using the CdNC signal obtained using the $B_3$ 410, one can perform pipeline tomography and check for oil pipeline obstructions.

The composition of crude oil may be similar to the following:

Carbon (mostly $^{12}C$, $^{13}C$) 83 to 85%;
Hydrogen (mostly $^1H$, $^2H$) 10 to 14%;
Nitrogen (mostly $^{14}N$) 0.1 to 2%;
Oxygen (mostly $^{16}O$, $^{17}O$, $^{18}O$) 0.05 to 1.5%;
Sulphur (mostly $^{32}S$, $^{33}S$, $^{34}S$, $^{36}S$) 0.05 to 6.0%;
Metals (mostly iron, nickel, copper, and vanadium) <0.1%.

Some of the crude oil components can have gamma ray emissions in the energy range of the $B_1$ 408. Such components may be, for example, isotopes nitrogen-14 ($^{14}N$), oxygen-18 ($^{18}O$) sulphur-32 ($^{32}S$), sulphur-33 ($^{33}S$), and sulphur-34 ($^{34}S$).

Similarly to the BNCT dose calculation described above, an intensity map of the signal from $B_1$ and a database such as the CapGam database, provided by the National Nuclear Data Center, Brookhaven National Laboratory, USA, can be used to estimate the composition of the oil.

The same elements that emit gamma rays in the energy range of $B_1$, can also emit gamma rays in the energy range of $B_4$. Some other elements may also emit in the $B_4$: e.g. isotopes carbon-13 ($^{13}C$), nitrogen-14 ($^{14}N$), oxygen-16 ($^{16}O$), oxygen-17 ($^{17}O$), oxygen-18 ($^{18}O$), sulphur-32 ($^{32}S$), sulphur-33 ($^{33}S$), sulphur-34 ($^{34}S$), and sulphur-36 ($^{36}S$). Whereas $^{16}O$ and $^{32}S$ may have the strongest gamma emission in the energy range of $B_4$.

Similarly to the BNCT dose calculation described above, the $N_4$ can be used to improve the intensity information in another energy range, such as $B_1$.

For any embodiment described herein, the accuracy can further be improved by adding more energy ranges. For example, energy ranges $B_1$-$B_4$ may be divided into sub-ranges. Thus, the resolution of each energy range may be increased.

In some embodiments, the photon counts $N_1$-$N_4$ may be compared to a corresponding reference value. The change compared to the reference value may be used to obtain information about the material 203. The reference value may be obtained, for example, by calibrating the system 100 without the material 203 in the system 100. Such calibration may be performed, for example, periodically.

The embodiments related to BNCT and NDT described above are only exemplary applications for the imaging method 100 and/or the imaging system 200. The imaging method 100 and/or the imaging system 200 may also be used in other applications, such as security applications. For example, the imaging method 100 and/or the imaging system 200 may be used to check the luggage for explosives or volatile compounds at locations of critical infrastructure.

Any range or device value given herein may be extended or altered without losing the effect sought. Also any embodiment may be combined with another embodiment unless explicitly disallowed.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item may refer to one or more of those items.

The steps of the methods described herein may be carried out in any suitable order, or simultaneously where appropriate. Additionally, individual blocks may be deleted from any of the methods without departing from the spirit and scope of the subject matter described herein. Aspects of any of the embodiments described above may be combined with aspects of any of the other embodiments described to form further embodiments without losing the effect sought.

The term 'comprising' is used herein to mean including the method, blocks or elements identified, but that such blocks or elements do not comprise an exclusive list and a method or apparatus may contain additional blocks or elements.

It will be understood that the above description is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

The invention claimed is:

1. An imaging method, comprising:
emitting neutrons into a material, wherein the material converts at least part of the emitted neutrons into a first plurality of gamma ray photons, and wherein at least part of the emitted neutrons pass through the material;
converting at least part of the neutrons passed through the material into a second plurality of gamma ray photons;
detecting a number of gamma ray photons, $N_1$, in a first energy range, $B_1$, wherein the $B_1$ is comprised in a range 0-511 kiloelectronvolts, keV;
detecting a number of gamma ray photons, $N_2$, in a second energy range, $B_2$, wherein the $B_2$ is comprised in a range 500-520 keV;
detecting a number of gamma ray photons, $N_3$, in a third energy range, $B_3$, wherein the $B_3$ is comprised in a range 511-660 keV;
detecting a number of gamma ray photons, $N_4$, in a fourth energy range, $B_4$, wherein a lower boundary of the $B_4$ is greater than or equal to 650 keV; and
deducing at least one property of the material based on the $N_1$, the $N_2$, the $N_3$, and the $N_4$.

2. The imaging method according to claim 1, wherein:
the $B_1$ is comprised in a range 100-509 keV;
the $B_2$ is comprised in a range 509-516 keV;
the $B_3$ is comprised in a range 516-656 keV; and/or
the lower boundary of the $B_4$ is greater than or equal to 656 keV.

3. The imaging method according claim 1, wherein the $N_2$ corresponds to a number of annihilation events.

4. The imaging method according to claim 1, wherein the deducing at least one property of the material comprises:
identifying at least one element in the material based on the $N_1$, the $N_2$, the $N_3$, and the $N_4$.

5. The imaging method according to claim 4, wherein the deducing at least one property of the material further comprises:
deducing a concentration of the at least one element in the material based on the $N_1$, the $N_2$, the $N_3$, and the $N_4$.

6. The imaging method according to claim 1, wherein the deducing at least one property of the material comprises:
deducing a number of neutrons passed through the material based on $N_3$.

7. The imaging method according to claim 1, wherein the material comprises boron-10, and the deducing at least one property of the material comprises:
deducing a boron-10 concentration in the material based on the $N_1$, the $N_2$, the $N_3$, and the $N_4$.

8. The imaging method according to claim 7, further comprising:
calculating a radiation dosage to a tumour in a patient for boron neutron capture therapy based on the boron-10 concentration.

9. The imaging method according to claim 1, wherein at least one property of the material comprises a structural property of the material.

10. The imaging method according to claim 1, wherein the material comprises oil, and wherein the deducing at least one property of the material comprises:
deducing a chemical composition of the oil based on the $N_1$, the $N_2$, the $N_3$, and the $N_4$.

11. The imaging method according to claim 1, wherein the converting at least part of the neutrons passed through the material into the second plurality of gamma ray photons is performed using a detector comprising cadmium.

12. The imaging method according to claim 11, wherein the detector comprises at least one of:
cadmium telluride;
cadmium zinc telluride;
cadmium magnesium telluride; and
cadmium zinc telluride selenide.

13. An imaging system, comprising:
a neutron source, configured to:
emit neutrons into a material, wherein the material converts at least part of the emitted neutrons into a first plurality of gamma ray photons, and wherein at least part of the emitted neutrons pass through the material;
a detector, configured to:
convert at least part of the neutrons passed through the material into a second plurality of gamma ray photons;
detect a number of gamma ray photons, $N_1$, in a first energy range, $B_1$, wherein the $B_1$ is comprised in a range 0-511 kiloelectronvolts, keV;
detect a number of gamma ray photons, $N_2$, in a second energy range, $B_2$, wherein the $B_2$ is comprised in a range 500-520 keV;
detect a number of gamma ray photons, $N_3$, in a third energy range, $B_3$, wherein the $B_3$ is comprised in a range 511-660 keV; and
detect a number of gamma ray photons, $N_4$, in a fourth energy range, $B_4$, wherein a lower boundary of the $B_4$ is greater than or equal to 650 keV; and
a computing device, configured to:
deduce at least one property of the material based on the $N_1$, the $N_2$, the $N_3$, and the $N_4$.

14. The imaging system according to claim 13 wherein the detector comprises a direct conversion material comprising cadmium.

15. The imaging system according to claim 14, wherein the direct conversion material comprises at least one of:
cadmium telluride;
cadmium zinc telluride;
cadmium magnesium telluride; or
cadmium zinc telluride selenide.

* * * * *